US006899456B2

(12) United States Patent
Sundaram et al.

(10) Patent No.: US 6,899,456 B2
(45) Date of Patent: *May 31, 2005

(54) GLIDE HEAD FOR ASPERITY DETECTION

(75) Inventors: Ramesh Sundaram, Fremont, CA (US); Wei H. Yao, Fremont, CA (US)

(73) Assignee: Seagate Technology LLC, Scotts Valley, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 126 days.

(21) Appl. No.: 09/176,580

(22) Filed: Oct. 21, 1998

(65) Prior Publication Data

US 2002/0018508 A1 Feb. 14, 2002

Related U.S. Application Data

(60) Provisional application No. 60/082,244, filed on Apr. 16, 1998.

(51) Int. Cl.$^7$ ............................ G11B 5/127; G11B 5/40; G01B 5/207; G01N 25/00
(52) U.S. Cl. ............................... 374/4; 374/7; 374/208; 73/105; 29/603.12; 29/603.16
(58) Field of Search ........................ 374/4, 7; 73/105; 29/603.12, 603.16, 603.07, 595

(56) References Cited

U.S. PATENT DOCUMENTS

| | | | |
|---|---|---|---|
| 4,333,229 A | * | 6/1982 | Ellenberger .................. 29/603 |
| 4,532,802 A | | 8/1985 | Yeack-Scranton et al. ..... 73/432 |
| 4,564,585 A | | 1/1986 | Blaske et al. ................ 430/313 |
| 4,635,139 A | * | 1/1987 | Nguyen et al. ............... 368/25 |
| 4,674,875 A | | 6/1987 | Koizumi ..................... 356/237 |
| 4,816,743 A | | 3/1989 | Harms et al. ................ 324/56 |
| 4,881,136 A | | 11/1989 | Shiraishi et al. .............. 360/25 |
| 4,942,609 A | | 7/1990 | Meyer ........................ 360/25 |
| 4,961,121 A | | 10/1990 | Astheimer et al. .......... 360/103 |
| 5,137,750 A | | 8/1992 | Amin et al. ................ 427/116 |

(Continued)

FOREIGN PATENT DOCUMENTS

| | | |
|---|---|---|
| EP | 442 660 A2 | 2/1991 |
| EP | 0 442 660 A2 | 8/1991 |
| JP | 54-023517 | 2/1979 |
| JP | 56-107363 | 8/1981 |
| JP | 59-193580 | 2/1984 |
| JP | 04-245054 | 1/1992 |
| JP | 08-069674 | 3/1996 |
| JP | 08-212740 | 8/1996 |
| JP | 08-279132 | 10/1996 |
| JP | 08-287440 | 11/1996 |

OTHER PUBLICATIONS

IBM Technical Disclosure Bulletin, vol. 26, No. 3A, Aug. 1983.*
"Thin Film Magnetic Heads", *IBM Technical Disclosure Bulletin*, May 1979.
"Dimple/Air Bearing Surface Alignment Process", *IBM Technical Disclosure Bulletin*, Mar. 1992.
U.S. Appl. No. 09/176,352, filed date Oct. 21, 1998.

*Primary Examiner*—Gail Verbitsky
(74) *Attorney, Agent, or Firm*—Westman, Champlin & Kelly

(57) ABSTRACT

Glide heads for the detection of asperities on a storage disc have a thermal transducer oriented along the air bearing surface. The thermal transducer generally is in electrical contact with a circuit to measure the electrical resistance of the thermal transducer. Preferred methods of depositing the thermal transducer involve the deposition of the thermal transducer on the smooth surface of a wafer prior to the slicing of individual sliders.

6 Claims, 4 Drawing Sheets

U.S. PATENT DOCUMENTS

| | | | |
|---|---|---|---|
| 5,177,860 A | | 1/1993 | Yura et al. ..................... 29/60 |
| 5,270,882 A | | 12/1993 | Jove et al. ..................... 360/67 |
| 5,372,427 A | * | 12/1994 | Padovani et al. ........... 374/185 |
| 5,423,111 A | | 6/1995 | Mori ............................ 29/90 |
| 5,423,207 A | * | 6/1995 | Flechsig et al. .............. 73/105 |
| 5,424,638 A | | 6/1995 | Huber ........................ 324/212 |
| 5,452,166 A | | 9/1995 | Aylwin et al. ............... 360/126 |
| 5,509,554 A | | 4/1996 | Samuelson et al. ........... 216/22 |
| 5,527,110 A | | 6/1996 | Abraham et al. .............. 374/5 |
| 5,528,922 A | | 6/1996 | Baumgart et al. ................ 73/1 |
| 5,537,034 A | | 7/1996 | Lewis ........................ 224/212 |
| 5,559,051 A | | 9/1996 | Voldman et al. .............. 437/51 |
| 5,588,199 A | | 12/1996 | Krounbi et al. ............ 29/603.1 |
| 5,603,156 A | | 2/1997 | Biskeborn et al. ........ 29/603.16 |
| 5,605,154 A | | 2/1997 | Ries et al. ............. 128/660.08 |
| 5,612,839 A | | 3/1997 | Jacques ...................... 360/103 |
| 5,689,064 A | * | 11/1997 | Kennedy et al. .............. 73/105 |
| 5,696,643 A | | 12/1997 | Tsuwako et al. ......... 360/73.03 |
| 5,718,035 A | * | 2/1998 | Yamanaka et al. ......... 29/603.1 |
| 5,735,036 A | | 4/1998 | Barr et al. ................ 29/603.12 |
| 5,761,005 A | | 6/1998 | McKay et al. .............. 360/104 |
| 5,771,571 A | | 6/1998 | Voldman et al. .......... 29/603.12 |
| 5,808,184 A | | 9/1998 | Boutaghou et al. ........... 73/105 |
| 5,817,931 A | | 10/1998 | Boutaghou .................... 73/105 |
| 5,818,592 A | * | 10/1998 | Womack et al. ............. 356/357 |
| 5,825,181 A | | 10/1998 | Schaenzer et al. .......... 324/212 |
| 5,864,054 A | * | 1/1999 | Smith, Jr. ..................... 73/105 |
| 6,003,364 A | * | 12/1999 | Yao et al. ...................... 73/105 |
| 6,071,007 A | * | 6/2000 | Schaenzer et al. ............. 374/7 |
| 6,073,337 A | | 6/2000 | Strom ..................... 29/603.12 |
| 6,181,520 B1 | * | 1/2001 | Fukuda .................. 360/244.1 |
| 6,234,599 B1 | * | 5/2001 | Ishinaga et al. ............. 347/14 |
| 6,262,572 B1 | * | 7/2001 | Franco et al. ............... 324/212 |
| 6,360,428 B1 | * | 3/2002 | Sundaram et al. ....... 29/603.12 |
| 6,619,105 B1 | * | 9/2003 | Yao et al. ..................... 73/105 |
| 6,623,652 B1 | * | 9/2003 | Hsiao et al. .................. 216/22 |
| 6,712,985 B2 | * | 3/2004 | Biskeborn .................... 216/22 |
| 2002/0040595 A1 | * | 4/2002 | Sundaram et al. ............ 73/105 |

\* cited by examiner

FIG. 8
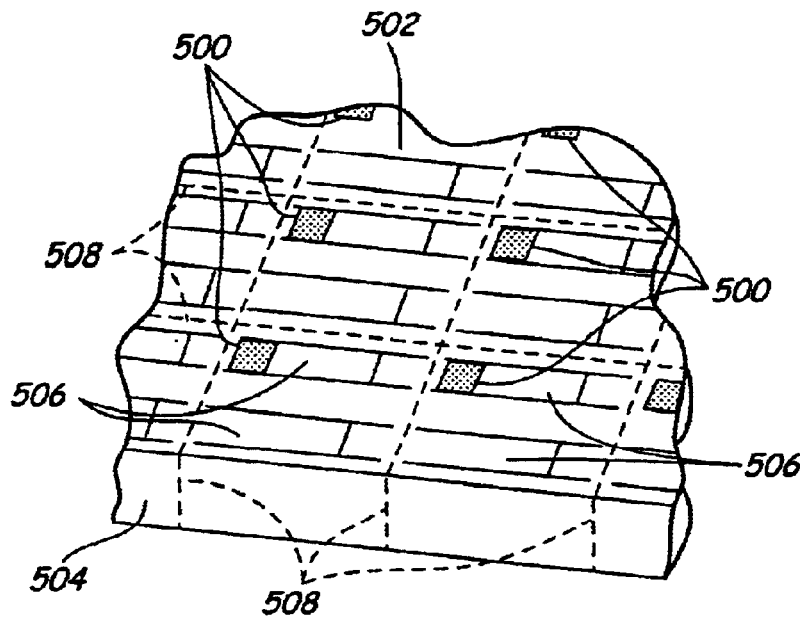
FIG. 9
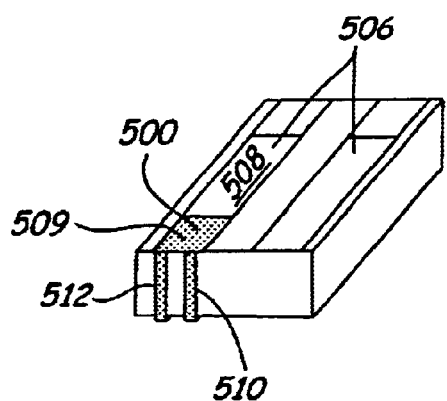
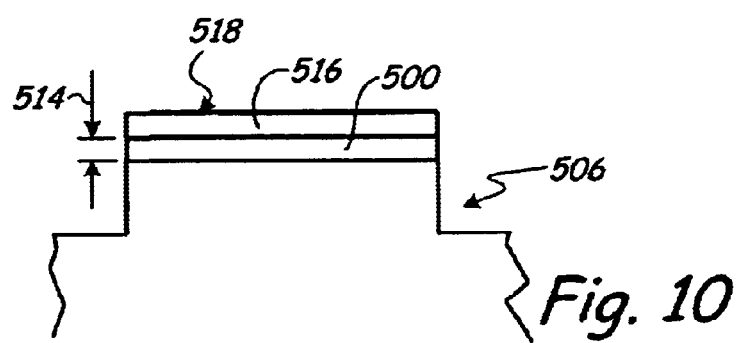
Fig. 10

GLIDE HEAD FOR ASPERITY DETECTION

CROSS REFERENCE TO RELATED APPLICATIONS

The present application claims priority to provisional patent application Ser. No. 60/082,244, entitled "A Novel Glide Head," filed on Apr. 16, 1998.

BACKGROUND OF THE INVENTION

The present invention relates generally to glide heads for evaluating glide quality of a disc surface, and to related methods. More particularly, the present invention relates to a glide head with a thermal transducer for detecting defects on a disc surface.

Disc drives are used for storing information, typically as magnetically encoded data, and more recently as optically encoded data, on a disc surface. The storage and retrieval operations generally involve "flying" a read and/or write head over the surface. As storage densities increase, the fly height of the heads over the disc surfaces generally are decreased. Consequently, defect heights on the discs must decrease proportionally to reduce or eliminate contacts between the head and disc that could damage the head, the disc or both.

Glide tests are used to determine if a given disc meets the required glide quality. The glide quality of a disc is related to the disc smoothness, although other defects also may alter glide quality. In particular, tests are used by computer disc manufacturers to control and assure the quality of the disc media. Generally, all hard drive discs are tested before shipment. During a glide test, the test head or slider flies over a disc surface generally at a predetermined clearance from the disc surface, known as the glide height or fly height. The glide head or slider includes a transducer that detects interactions between the disc and the glide head due to defects on the disc surface.

The glide heads are selectively moved under the control of electronic circuitry to any one of a plurality of circular, concentric data tracks on the disc surface by an actuator device. Each slider body includes an air bearing surface (ABS). As the disc rotates, the disc drags air beneath the ABS, which develops a lifting force that causes the glide head to lift and fly above the disc surface. Glide heads generally are designed to have a fly height that is sensitive to the linear velocity of the disc surface relative to the glide head. For example, to detect smaller defects on a disc surface, the disc velocity can be decreased to decrease the fly height of the glide head.

A transducer can be used to detect contacts between the glide head and defects. Generally, piezoelectric transducers are used to detect vibrations that result from contact between a glide head and a disc defect. Using glide heads, the process of mapping disc defects while changing the fly height of the head requires several scans at different head fly heights to map the entire range of defects. As the speed is changed, the response of the specially designed glide head also changes. For example, if the speed is reduced, the energy of the impact is reduced, thus making it more difficult to calibrate to the defect size and height.

SUMMARY OF THE INVENTION

In one aspect, the invention features an asperity detection slider including an air bearing surface and a thermal transducer. The thermal transducer is generally planar and is oriented along the air-bearing surface.

In another aspect the invention features, a method of producing an asperity detection slider, the method including depositing a thermal transducer along an air bearing surface of the slider.

BRIEF DESCRIPTION OF THE DRAWINGS

FIG. 9 is a schematic, perspective view of a slider with a thermal transducer along a rail on the air bearing surface and electrically conductive pads deposited on a rear edge prior to the addition of protective material over the pads.

FIG. 10 illustrates a raised bearing surface or rail including a thermal transducer and protective layer.

DETAILED DESCRIPTION OF THE PREFERRED EMBODIMENTS

Figure 1:
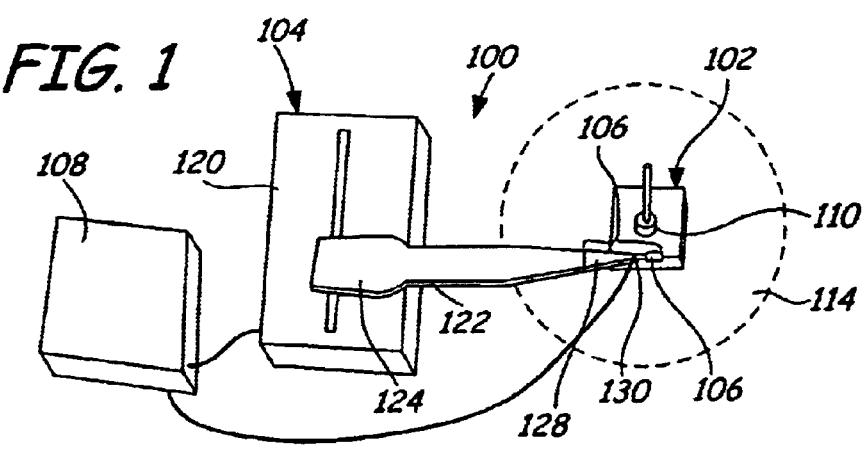
FIG. 1 is a schematic, top perspective view of a glide tester incorporating an improved glide head, where a disc is shown with phantom lines such that structure below the disc is visible.

By placing a thermal transducer as an defect/asperity sensor on the air bearing surface of a slider/glide head, glide testing can be performed efficiently with a high sensitivity. After a defect strikes the thermal transducer, a resistance spike is detected to provide a signature that a defect has contacted the glide head. Furthermore, thermal transducers oriented along the air bearing surface can present a large contact area on the air bearing surface. Thus, a glide test can be performed efficiently since asperities with a greater range of heights strike the thermal transducer when contacting the glide head. A plurality of thermal transducers on the air bearing surface can be used to assess the distribution of defect heights.

Glide tests performed with piezoelectric (PZT) transducers can be accomplished efficiently since defects with a wide range of heights are detected in one pass over a section of the disc. It is believed, though, that glide heads with PZT transducers may give positive readings when defects pass near the glide head even when they do not strike. Thus, PZT based glide heads may result in false positive readings for defects.

Magnetoresistive (MR) type sensors used in read/write heads can operate as thermal transducers. In contrast with defect sensors placed on the air bearing surface, MR sensors in read/write heads are located on a side of the slider adjacent the air bearing surface and have only an edge of the MR sensor in contact with the air bearing surface. After contact with an defect, the heat generated by the contact changes the resistive properties of the MR sensor. As a result, the measurement of the resistance of the MR transducer biased by a constant current source is distorted by a spike and subsequent decay. Because of the narrow profile along the air bearing surface presented by the MR sensor in a read/write head, few defects will strike the glide head at the MR sensor with the MR sensor at the trailing edge side. Collisions with defects that strike such a glide head away from the MR sensor may not produce a voltage spike in the resistance measurement.

Thus, thermal defect detection methods using either MR read/write heads having a narrow MR sensor track width, or asperity detection sliders adapted from MR read/write head designs having an increased MR sensor track width have inherent limitations. Using MR read/write heads, with track widths typically less than 2.5 $\mu$M, the time for a full surface scan is extremely time consuming. Furthermore, standard MR read/write heads of the type used in disc drive systems are designed to reduce sensitivity to thermal asperity response by having increased fly heights and/or MR transducer recessed with respect to the air bearing surface. Specially designed thermal asperity heads can reduce the surface scan time and increase the thermal asperity response by using a somewhat wider MR sensor track, for example, 60 $\mu$M. This wider MR sensor track still only covers a very small portion of the slider air bearing surface.

It is believed that thermal asperity detectors do not respond to near misses between a defect and the glide head. In particular, contact between the thermal transducer and a defect produces a characteristic resistance spike that may not be produced by contact between other portions of the slider and the defect. Thus, thermal transducers by their nature are inherently very sensitive to contact with a defect, while rarely giving a false positive reading. Thermal transducers placed on the air-bearing surface can take advantage of both a high sensitivity with respect to detecting actual contact with an asperity and an ability to detect simultaneously a larger range of defect heights. In this way, the glide test can be performed with an efficiency comparable to PZT based glide tests while taking advantage of the high sensitivity and specificity obtained with a thermal transducer.

Under previous practices for slider/glide head production, one of the cut surfaces of the slider formed from a wafer is formed into the air-bearing surface. If a cut surface is formed into the air bearing surface, a thermal transducer formed along an edge of the slider can be placed on the wafer prior to cutting the slider from the wafer. A novel approach to the production of glide heads involves using a very smooth surface of the wafer as the air bearing surface. The cut edges of the wafer become the sides of the slider.

Using this alternative slider production procedure, thermal transducers can be placed on the air-bearing surface at the wafer level prior to cutting the individual sliders. Thermal transducer application on the air bearing surface provides for the performance of many processing steps at the wafer level. In particular, the placement of the thermal transducer on the air bearing surface can be performed more efficiently at the wafer level prior to cutting individual sliders from the wafer.

The thermal transducers are made from materials that alter their electrical resistance in response to a temperature change. To complete the asperity detector, the thermal transducer is connected to a circuit that provides for the measurement of the electrical resistance of the material in the transducer on the air bearing surface. To form the electrical circuit, electrical conducting pads can be placed along an edge of the slider to connect electrically the air bearing surface with the top surface of the slider. A particular thermal transducer is connected to two electrical pads to form a circuit through the transducer. The electrical circuit for resistance measurement is completed with connections to the electrical pads at the top of the slider body.

The air bearing surface of the slider generally includes contoured portions such as rails for aerodynamic performance. The thermal transducers generally are placed on an extended portion of the surface such that they will provide the point of contact with an asperity. A single large transducer can provide for defect detection over a larger range of defect heights. The use of multiple thermal transducers can provide for grading of asperities, as described further below. Thus, selection of the number and placement of the thermal transducers involves a balance between the processing complexity and the amount of information desired about the nature of the asperities. In preferred embodiment, the one or more thermal transducers cover an area of the air bearing surface from about 0.05 mm$^2$ to about 5.0 mm$^2$.

Referring to FIG. 1, a glide tester 100 includes a glide spinstand 102, an arm assembly drive 104, a suspension/glide head assembly 106 and a controller 108. Glide spinstand 102 includes a spindle motor 110 and disc 114, shown in phantom lines. Spindle motor 110 supports and spins disc 114. Arm assembly drive 104 has a motorized drive 120 and an arm 122. Arm 122 has a support portion 124 that connects with motorized drive 120 and an extension portion 126 that extends over disc 114. Motorized drive 120 moves arm 122 either by lateral motion or by rotational motion to alter the radial position of suspension/glide head assembly 106 along a disc 114 mounted on glide spinstand 102.

Suspension/glide head assembly 106 generally includes suspension 128, gimbal 130 and glide head 132. Suspension 128 connects with arm 122. Glide head 132 is connected to suspension 128 by way of gimbal 130. Suspension 128 and gimbal 130 can have a variety of designs including conventional structures.

Controller 108 is connected to arm assembly drive 104 and spindle motor 110. Controller 108 correlates the position of arm 126 with the rotational speed of the spindle motor to maintain an approximately constant linear speed of slider 132 relative to the disc surface. Also, controller 108 correlates impact information detected by glide head 132 with a defect location on disc 114.

Figure 2:
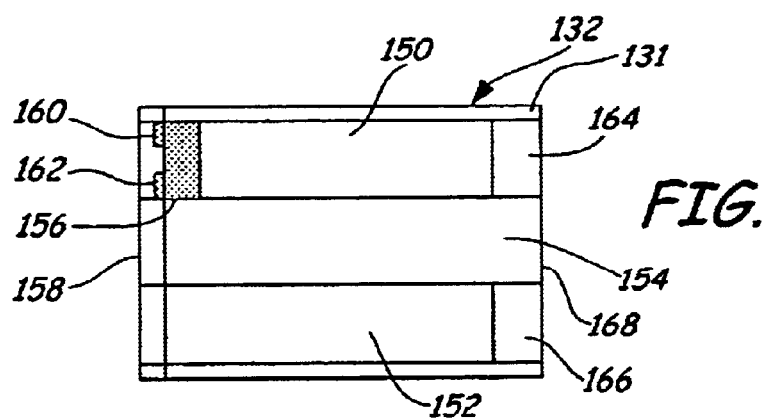
FIG. 2 is a bottom view of an embodiment of an slider with a thermal transducer located on the air bearing surface.

An embodiment of a glide head/slider 132 is depicted in FIG. 2. Glide head 132 includes a glide body 131 and two rails 150, 152 on air bearing surface 154. A thermal transducer 156 is located on rail 150. Thermal transducer 156 is located near rear edge 158 of glide head 132. Electrically conducting pads 160, 162 electrical contact between thermal transducer 156 and the top of glide head 132. Pads 160, 162 are connected to a measurement circuit at the top of the glide head such that the electrical resistance of thermal transducer 156 can be monitored. To improve the aerodynamic performance, steps 164, 166 are located near front edge 168 of glide head 132. The contoured features on the air bearing surface can be varied to achieve a desired aerodynamic performance of the glide head.

Thermal transducer 156 generally is made from material with an electrical resistance that varies with temperature. For example, materials such as NiFe alloy used to form magnetoresistive transducers also exhibit a thermal resistance effect. Preferred materials for producing the thermal transducers have a resistance that is relatively insensitive to magnetic fields since the defect measurement should not be sensitive to the magnetic field near the glide head. Preferred materials for forming the thermal transducer include, for example, nickel (Ni). Electrically conductive pads 160, 162 generally are made of conducting metal, alloy or metal compound. Electrically conductive pads 160, 162 are made preferably from gold.

Figure 3:
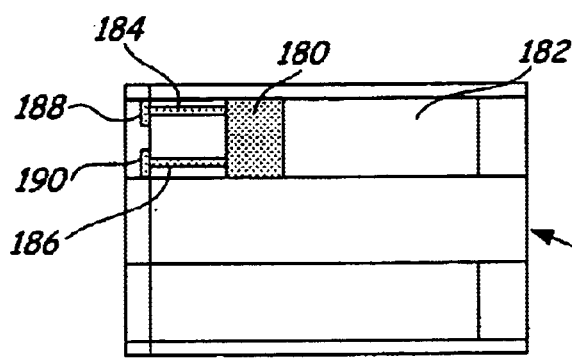
FIG. 3 is a bottom view of another embodiment of an slider where a thermal transducer is located on the air bearing surface away from the slider's rear edge.

The back edge or trailing edge of glide head 132 generally flies closer to the surface of the disc than the front edge or leading edge. The pitch of glide head 132 is due to aerodynamic forces. Therefore, placement of the thermal transducer near the rear edge or trailing edge of the glide head provides for the detection of smaller asperities for a given fly height. Nevertheless, if desired the thermal transducer can be placed away from the rear edge or trailing edge. Such an alternative embodiment is depicted in FIG. 3. Thermal transducer 180 is located on rail 182. Electrical conduction strips 184, 186 provide for electrical conduction between thermal transducer 180 and electrical conduction pads 188, 190. Electrical conduction pads 188, 190 provide a path of electrical conduction between strips 184, 186 and the top of glide head 132. Electrical conduction strips 184, 186 can be produced from electrically conductive metal, alloys, metal compounds or combinations thereof.

Figure 4:
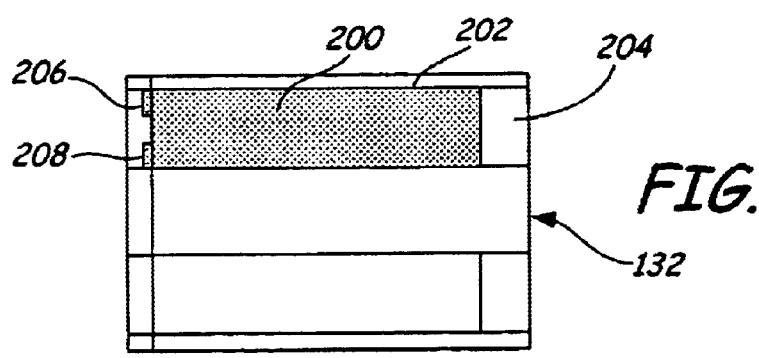
FIG. 4 is a bottom view of an embodiment of an slider where a thermal transducer covers a substantial portion of a rail on the air bearing surface.

If the thermal transducers cover a substantial portion of the length of the glide head, defects with a wide range of heights strike the thermal transducers to produce a spike in the resistance of the transducer rather than striking a portion of the air bearing surface away from a transducer. Thus, another alternative embodiment of a glide head 132 is shown in FIG. 4. Thermal transducer 200 covers substantially all of rail 202 up to step 204. Thermal transducer 200 is in electrical contact with electrically conductive pads 206, 208.

A plurality of thermal transducers can be used on a single glide head. In preferred embodiments, a plurality of thermal transducers cover a substantial portion of the length of the glide head. In particular, the plurality of transducers can cover a substantial portion of a rail or other contour on the air bearing surface. The use of a suitably placed plurality of thermal transducers provide for the grading of defects by height. In other words, defects with different ranges of heights strike the glide head at different portions of the air bearing surface due to the pitch of the slide during use. Identification of the transducer that is struck indicates that the asperity has a height within a particular range.

Figure 5:
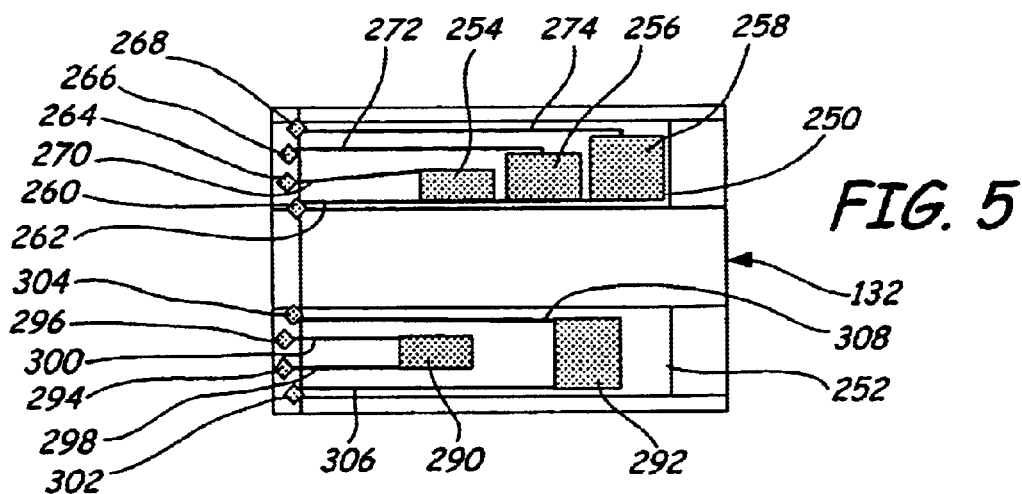
FIG. 5 is a bottom view of a slider having two different configurations of multiple thermal transducers located along a rail on the air bearing surface.

Two embodiments for the placement of multiple transducers are indicated in FIG. 5. In the slider 132 of FIG. 5, rail 250 has one configuration of multiple transducers while rail 252 has a second configuration. The placement of thermal transducers on more than one rail or other contour provides for the simultaneous detection of asperities on two portions of the disc surface. The motion of the slider across the disc surface can be adjusted accordingly.

Thermal transducers 254, 256, 258 are located on rail 250. Pad 260 and strip 262 provide electrical contact to a common ground for transducers 254, 256, 258. The use of a common ground reduces the space needed for electrical conduction strips and reduces processing related to the deposition of conduction strips. Pads 264, 266, 268 and strips 270, 272, 274 provide electrical conduction to transducers 254, 256, 258, respectively, for resistance measurements.

Thermal transducers 290, 292 are located on rail 252. Pads 294, 296 and conduction strips 298, 300 provide electrical connections to transducer 290. Similarly, pads 302, 304 and conduction strips 306, 308 provide electrical connections to transducer 292. In contrast with transducers 254, 256, 258, transducers 290, 292 do not share a common ground.

Figure 6:
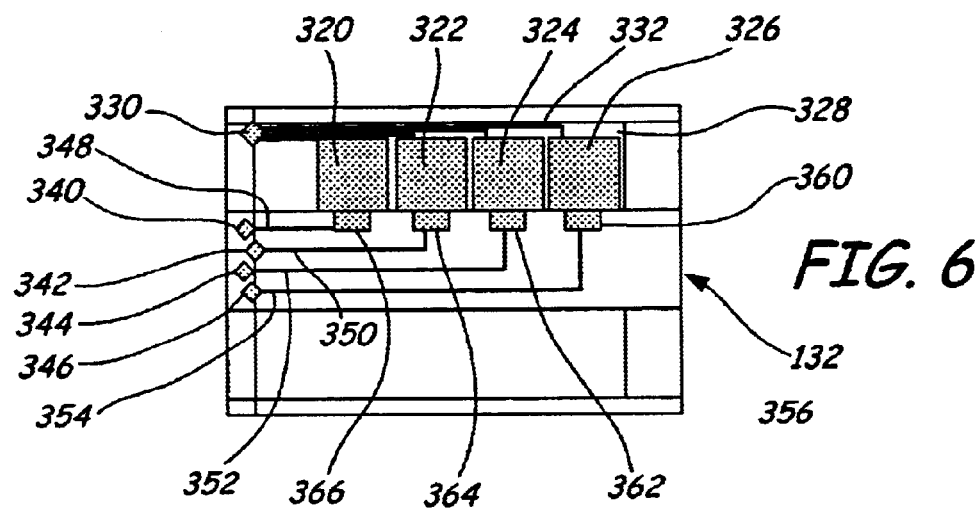
FIG. 6 is a bottom view of an slider having an alternative configuration of multiple thermal transducers located along a rail on the air bearing surface.

An alternative configuration of slider 132 having multiple thermal transducers is depicted in FIG. 6. Thermal transducers 320, 322, 324, 326 are located on rail 328. Transducers 320, 322, 324, 326 share a common electrical ground provided by pad 330 and conductive strip 332. Pads 340, 342, 344, 346 provide the remaining electrical connections for transducers 320, 322, 324, 326, respectively, with the top of slider 132.

Pads 340, 342, 344, 346 are in electrical contact with conductive strips 348, 350, 352, 354. Conductive strips 348, 350, 352, 354 are located on plateau 356. Since transducers 320, 322, 324, 326 are located on rail 328, electrical connection between the transducers and strips 348, 350, 352, 354 is established by electrically conductive pads 360, 362, 364, 366. The placement of conductive strips 248, 350, 352, 354 on plateau 356 provides for the coverage of a greater portion of the surface of rail 328 with thermal transducers, although additional processing may be required to produce pads 360, 362, 364, 368 that provide electrical conduction between plateau 356 and rail 328.

A slider with a thermal transducer on the air bearing surface can also have one or more additional transducers for the detection of defects. The use of multiple types of transducers provides for a comparison between measurements made with different types and/or configurations of transducers. For example, thermal transducers which are particularly sensitive to actual strikes with an asperity can be used to evaluate whether piezoelectric transducers produce false positive signals from near misses with asperities.

Moreover, multiple types of transducers for detecting defects can be used to provide more accurate defect detection. For example, the measurements from multiple types of transducers can be compared with a matrix of threshold values to evaluate whether a defect has been struck. In other words, if one transducer produces a particular reading, a corresponding threshold value can be used for the other transducer to evaluate whether or not a defect was struck. A correlation of the measurements from the multiple transducers should reduce the number of false positive readings and false negative readings. Thus, measurements can be made with a greater confidence level.

Figure 7:
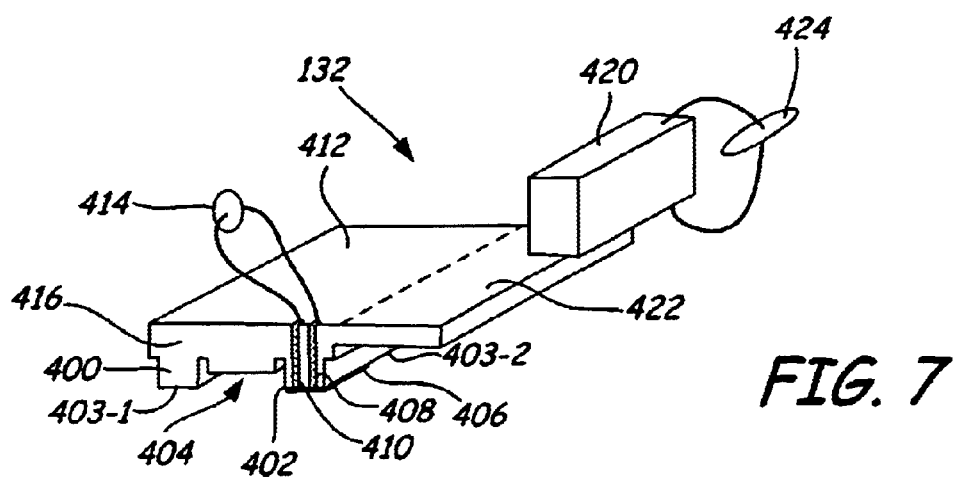
FIG. 7 is a schematic perspective view of an slider having both a thermal transducer and a piezoelectric transducer.
Figures 1, 7:
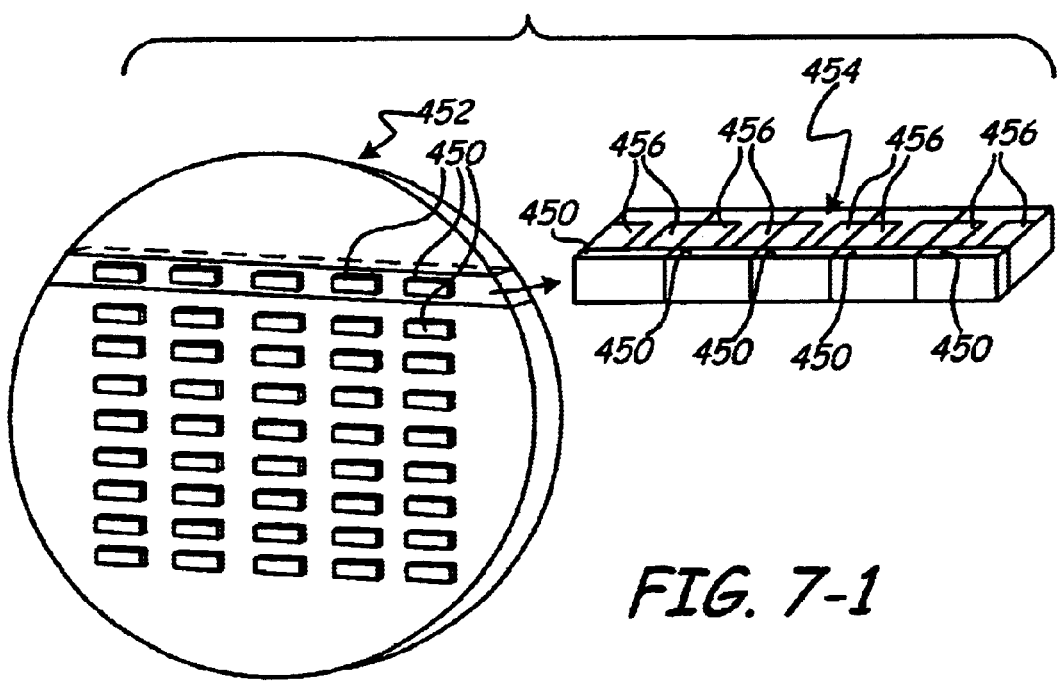

An embodiment of glide head 132 with different types of defect detecting transducers is depicted in FIG. 7. Glide head 132 includes rails 400, 402 along air bearing surface 404 which form raised bearing surfaces 403-1, 403-2 as shown in FIG. 7 which are elevated above surface 404. Thermal transducer 406 is located on rail 402 along the raised bearing surface 403-2. Electrically conductive pads 408, 410 provide electrical conduction between transducer 406 and the top surface 412 of glide head 132. Pads 408, 410 are connected to resistance measurement circuit 414 for the evaluation of changes in resistance of the transducer 406. Pads 408, 410 are located along or near rear edge 416 of glide head 132. Piezoelectric transducer 420 is located on wing 422 along top surface 412. Piezoelectric transducer 420 is connected to measurement circuit 424.

As previously described on page 6 of the specification, in previous practices, transducers 450 were formed on a wafer 452 as illustrated in FIG. 7–1. The wafer 452 is cut to form a cut surface 454 and the air bearing surfaces 456 IS contoured or formed on the cut surface 454 so that the thermal transducer 450 is formed along an edge of the slider as shown prior to cutting and fabrication of the air bearing surfaces 456. Thus as described in previous practices, the transducer is deposited at the wafer level prior to fabrication of the air bearing surface 456 and thereafter the wafer 452 is cut to form the air bearing surface 456 on a cut surface 454 so that the transducer 450 is formed along the edge of the slider.

Figures 1, 8:
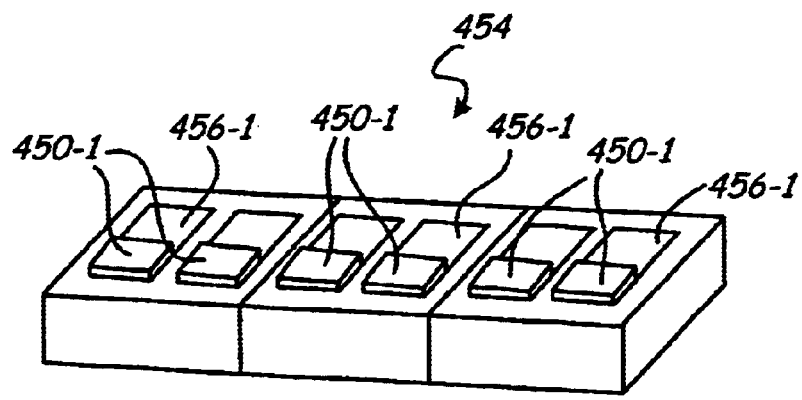
FIG. 8 is a schematic, fragmentary perspective view of a wafer with thermal transducers located on the surface of the wafer at locations that are contoured to be an air bearing surface of the ultimate sliders.

The present invention relates to fabrication of the transducer on the contoured or air bearing surface. In the embodiment shown in FIG. 8, the air bearing surface or contoured surfaces 506 are fabricated at the wafer level or on the wafer and the thermal transducers 500 are also fabricated at the wafer level prior to slicing individual sliders as shown. Alternatively as shown in FIG. 8–1, air bearing surfaces 456-1 and transducers 450-1 are fabricated on a cut surface 454 of the wafer. Regardless of the particular embodiment for the placement and number of thermal transducers on the air bearing surface, the thermal transducers generally are formed on the air bearing surface following the contouring of the air bearing surface to form the gross shape of the air bearing surface in contrast to fabrication processes as illustrated in FIG. 7–1 where transducers 450 are deposited on a surface of the wafer 452 prior to cutting and fabrication of the air bearing surfaces 456. The thermal transducers can be deposited using any of the vacuum metal deposition techniques, such as sputtering. Conductive strips and conduction pads can be similarly deposited. Generally, the components are covered with a protective, electrically insulating layer such as diamond like carbon.

In one embodiment, where the air bearing surface and transducer is formed from a cut surface 454 of the wafer the electrically conductive pads can be deposited on the surface of the wafer prior to the slicing of the wafer. The pads are positioned on the wafer surface such that they are along the rear edge of the slider after the sliders are cut from the wafer as shown in FIG 9.

Following fabrication of the pads, the wafer is cut and the air bearing surface or cut surface is subjected to one or more stages of lapping (e.g., rough lap, smooth lap and crown lap) to smooth the surface. Lapping generally involves mechanical, chemical and/or mechanical/chemical polishing. Following a desired amount of lapping, the air bearing surface is contoured using thin layer deposition techniques, milling techniques such as ion milling, reactive ion milling or laser ablation, or a combination thereof. Following contouring, the thermal transducers and conductive strips are applied to the air bearing surface. A protective coating then can be applied, if desired.

As noted above, a preferred approach for the production of sliders with thermal transducers on the air bearing surface involves forming air bearing surfaces of the sliders at the wafer level such that the air bearing surface of the slider is formed from a surface of the wafer. Thus, a greater portion of the slider preparation is performed at the wafer level. In particular, the contouring of the air bearing surface and the placement of the thermal transducer is formed on the wafer prior to slicing the individual sliders as shown in FIG. 8. A portion of a wafer processed to produce sliders configured as shown in FIG. 2 is depicted in FIG. 8.

To form the sliders with the thermal transducers located on the air bearing surface (e.g. raised bearing surfaces), a plurality of thermal transducers 500 can be applied along the smooth surface 502 of wafer 504, as shown in FIG. 8. Thermal transducers 500 are located or formed on the raised bearing surfaces 508 of rails 506 contoured onto surface 502 or contoured surface to form a surface portion 509 extending along a portion of the raised surface 508 of rail 506 and a thickness portion 514 which forms a profile 518 of the contoured surface as illustrated in FIG. 10. Representative rails 506 are noted in FIG. 8. Alternatively, as previously explained, thermal transducers 500 can be formed on the raised contoured surface or rails of the air bearing surface on a bar sliced from the wafer. As shown in FIG. 10, the thermal transducers 500 can be covered with a protective layer 516, such as diamond, like carbon. Additional transducers such as a piezoelectric transducer also can be placed on the opposite surface of the wafer prior to the slicing into individual sliders.

After completing the desired processing of the wafer surfaces, the wafer is "diced" or sliced along cutting alleys 508, as indicated in FIG. 8, to produce cut faces. A first cut produces a set of rows with each row containing a plurality of sliders. A second cut along each row produces the individual sliders with four cut faces. A small quantity of material is lost along cutting alleys 508 during the slicing process.

Following slicing, any desired lapping of the cut edge is performed. In this processing approach, the electrically conductive pads 510, 512 of the slider are applied along the rear edge on the smoothed cut surface, as shown in FIG. 9. Additional details of the processing of sliders to produce an air bearing surface from a wafer surface is described in commonly assigned and simultaneously filed patent application Ser. No., 09/176,352 to Sundaram et al., entitled "GLIDE HEADS AND METHODS FOR MAKING GLIDE HEADS," incorporated herein by reference.

In order for asperity detection systems to be useful to test discs with different tolerances, glide heads generally are designed to have fly heights that depend on the linear velocity of the slider relative to the disc surface. The fly height is selected such that asperities larger than a tolerance value strike the glide head and preferably strike the thermal transducer. The linear velocity is set accordingly.

Tolerance levels for asperity detection are generally set lower than tolerances established for disc flatness in actual operation since fly heights during actual operation can be altered by additional factors including, for example, flutter of the spinning disc, spindle misalignment, high altitudes and temperature fluctuations. The glide head is swept across the disc surface at a suitable speed such that the relevant portions of the disc surface are examined with the glide head. The rotation rate generally is varied as the asperity detection slider is moved to different radial positions along the disc to maintain the relative linear velocity approximately constant.

The embodiments described above are intended to be illustrative and not limiting. Additional embodiments are within the claims below. Although the present invention has been described with reference to preferred embodiments, workers skilled in the art will recognize that changes may be made in form and detail without departing from the spirit and scope of the invention.

What is claimed is:

1. A glide head comprising:
   a glide body including a leading edge, a trailing edge and a contoured surface having a raised bearing surface elevated from a recessed bearing surface;
   at least one thermal transducer fabricated on the raised bearing surface having a surface portion extending along the raised bearing surface to form a glide interface to detect asperities and the at least one thermal transducer being in electrical contact with an electrically conductive pad proximate to the trailing edge of the glide body; and a conductive strip conductively coupled to the at least one thermal transducer and the conductive pad to provide an electrical contact between the at least one thermal transducer and the conductive pad.

2. A glide head comprising:

a glide body including a leading edge, a trailing edge and a contoured surface having a raised bearing surface elevated from a recessed bearing surface; and at least one thermal transducer fabricated on the raised bearing surface having a surface portion extending along the raised bearing surface to form a glide interface to detect asperities wherein the at least one thermal transducer extends along at least half of a length distance between the leading edge and the trailing edge of the glide body.

3. A glide head comprising:

a glide body including a leading edge, a trailing edge and a contoured surface having a raised bearing surface elevated from a recessed bearing surface; and a plurality of thermal transducers including at least one thermal transducer fabricated on the raised bearing surface having a surface portion extending along the raised bearing surface to form a glide interface to detect asperities wherein the plurality of thermal transducers comprise a first thermal transducer and a second thermal transducer and the first and second thermal transducers share a common electrical ground.

4. A glide head comprising:

a glide body including a leading edge, a trailing edge and a contoured surface having a raised bearing surface elevated from a recessed bearing surface; and a plurality of thermal transducers including at least one thermal transducer fabricated on the raised bearing surface having a surface portion extending along the raised bearing surface to form a glide interface to detect asperities wherein the plurality of thermal transducers are spaced along the raised bearing surface and the glide head further comprises electrically conductive strips in electrical contact with the plurality of thermal transducers, the strips being formed on the recessed bearing surface offset from the raised bearing surface.

5. A method of fabricating a glide head from a wafer comprising;

slicing a plurality of glide bodies from the wafer; and depositing thermal transducers on the plurality of glide bodies sliced from the wafer.

6. The method of claim 5 and further comprising:

fabricating air bearing surfaces on the plurality of glide bodies sliced from the wafer including a raised bearing surface and a recessed bearing surface prior to depositing the thermal transducers; and depositing the thermal transducers on the raised bearing surfaces of the plurality of glide bodies sliced from the wafer.

* * * * *